(12) United States Patent
Heo et al.

(10) Patent No.: US 9,548,820 B2
(45) Date of Patent: Jan. 17, 2017

(54) METHOD OF CONTROLLING ELECTRONIC APPARATUS AND ELECTRONIC APPARATUS USING THE SAME

(71) Applicant: Samsung Electronics Co., Ltd., Gyeonggi-do (KR)

(72) Inventors: Chang-Ryong Heo, Gyeonggi-do (KR); Kyung-Hee Lee, Gyeonggi-do (KR); Ken-Hyung Park, Gyeonggi-do (KR); Seong-Jun Song, Seoul (KR); Chi-Hyun Cho, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 5 days.

(21) Appl. No.: 14/330,406

(22) Filed: Jul. 14, 2014

(65) Prior Publication Data

US 2015/0017912 A1    Jan. 15, 2015

(30) Foreign Application Priority Data

Jul. 12, 2013  (KR) ........................ 10-2013-0082285

(51) Int. Cl.
| | | |
|---|---|---|
| *H04B 13/00* | (2006.01) | |
| *G06F 3/01* | (2006.01) | |
| *H04B 7/26* | (2006.01) | |
| *H04B 15/00* | (2006.01) | |
| *A61B 5/11* | (2006.01) | |
| *A61B 5/00* | (2006.01) | |

(52) U.S. Cl.
CPC .............. *H04B 13/005* (2013.01); *G06F 3/01* (2013.01); *H04B 7/26* (2013.01); *H04B 15/00* (2013.01); *A61B 5/1116* (2013.01); *A61B 5/6803* (2013.01)

(58) Field of Classification Search
CPC ................................................... H04B 13/005
See application file for complete search history.

(56) References Cited

U.S. PATENT DOCUMENTS

| | | | |
|---|---|---|---|
| 2005/0197575 | A1 | 9/2005 | Kondoh et al. |
| 2007/0211828 | A1* | 9/2007 | Song ...................... H03K 5/003 375/316 |
| 2007/0255141 | A1 | 11/2007 | Esenaliev et al. |
| 2008/0123599 | A1* | 5/2008 | Ishibashi .............. H04B 13/005 370/335 |
| 2008/0261523 | A1* | 10/2008 | Kubono ............... H04B 5/0012 455/41.1 |
| 2010/0040114 | A1* | 2/2010 | Kim ..................... H04B 13/005 375/130 |
| 2010/0304671 | A1* | 12/2010 | Hebiguchi .......... H04B 13/005 455/41.1 |

(Continued)

FOREIGN PATENT DOCUMENTS

| | | |
|---|---|---|
| EP | 1 458 122 | 9/2004 |
| KR | 1020110134758 | 12/2011 |

OTHER PUBLICATIONS

European Search Report dated Dec. 4, 2014 issued in counterpart application No. 14176798-1959.

*Primary Examiner* — David Bilodeau
(74) *Attorney, Agent, or Firm* — The Farrell Law Firm, P.C.

(57) ABSTRACT

A method of controlling an electronic apparatus and the electronic apparatus using the same are provided. The method includes transmitting signals through a medium, receiving and selecting some of the signals transmitted through the medium, and performing or setting a function according to the selected signals.

19 Claims, 15 Drawing Sheets

(56) References Cited

U.S. PATENT DOCUMENTS

2010/0324415 A1 12/2010 Drinan et al.
2011/0306303 A1 12/2011 Choi et al.
2012/0326833 A1 12/2012 Aichi et al.

* cited by examiner

| ACTION | SIGNAL PATTERN | MULTIMEDIA FUNCTION | E-BOOK FUNCTION |
|---|---|---|---|
| HOLD BOTH HANDS TOGETHER | | PAUSE | STORE RELEVANT PAGE WITH BOOKMARK |
| SEPARATE BOTH HANDS FROM EACH OTHER | | REPRODUCTION | FINISH STORING RELEVANT PAGE WITH BOOKMARK |
| CONTINUOUSLY TOUCH ARM UPWARDS | | INCREASE IN VOLUME REPRODUCE NEXT MEDIA | MOVE TO NEXT PAGE |
| CONTINUOUSLY TOUCH ARM DOWNWARDS | | REDUCTION IN VOLUME REPRODUCE PREVIOUS MEDIA | REPRODUCE PREVIOUS MEDIA |

FIG.10 methods # METHOD OF CONTROLLING ELECTRONIC APPARATUS AND ELECTRONIC APPARATUS USING THE SAME

PRIORITY

This application claims priority under 35 U.S.C. §119(a) to Korean Patent Application Serial No. 10-2013-0082285, which was filed in the Korean Intellectual Property Office on Jul. 12, 2013, the contents of which are incorporated herein by reference.

BACKGROUND OF THE INVENTION

1. Field of the Invention

The present invention relates generally to a method of controlling an electronic apparatus and the electronic apparatus using the same.

2. Description of the Related Art

Examples of methods for controlling an electronic apparatus include using a camera to recognize an action by the user and performing a particular operation according to a result of the recognition, recognizing the voice of a user and performing a particular operation according to a result of the recognition, and receiving a control command by an input means such as a touch pad and performing a particular operation according to the control command.

Using a camera to control an electronic apparatus consumes a large amount of power. Voice recognition is difficult in a noisy environment and requires quiet.

Therefore, there is a need for a method of controlling an electronic apparatus regardless of its environment, with low power consumption by using communication through a medium (hereinafter, medium communication), and the electronic apparatus using the same.

SUMMARY OF THE INVENTION

The present invention has been made to address at least the above-mentioned problems and/or disadvantages and to provide at least the advantages described below.

According to an aspect of the present invention, a method of controlling an electronic apparatus regardless of its environment, with low power consumption by using medium communication, and an electronic apparatus using the same, are provided.

According to one aspect of the present invention, a method of controlling an electronic apparatus is provided, including transmitting, by the electronic apparatus, a first signal to a first part of a medium; receiving, by the electronic apparatus, second signals through a second part of the medium, the second signals corresponding to the transmitted first signal; selecting, by the electronic apparatus, at least some signals from among the second signals; and performing, by the electronic apparatus, a function according to the selected at least some signals if such a function has been set.

According to another aspect of the present invention, an electronic apparatus is provided, including a transmission unit configured to transmit a first signal to a first part of a medium; a reception unit configured to receive second signals through a second part of the medium, the second signals corresponding to the first signal; and a control unit configured to select at least some signals from among the second signals and to set or perform a function according to the selected at least some signals.

According to yet another aspect of the present invention, a computer-readable non-transitory recording medium is provided, which stores a program for executing the steps of transmitting, by an electronic apparatus, a first signal to a first part of a medium; receiving, by the electronic apparatus, second signals through a second part of the medium, the second signals corresponding to the first signal; selecting, by the electronic apparatus, at least some signals from among the second signals; and performing, by the electronic apparatus, a function according to the selected at least some signals if such a function has been set, or setting, by the electronic apparatus, a function according to the selected at least some signals if such a function has not been set.

BRIEF DESCRIPTION OF THE DRAWINGS

The above and other aspects, features, and advantages of certain embodiments of the present invention will be more apparent from the following description taken in conjunction with the accompanying drawings, in which:

FIG. 10 is a view illustrating examples of functions being matched to patterns of signals, according to embodiments of the present invention.

DETAILED DESCRIPTION OF EMBODIMENTS OF THE PRESENT INVENTION

Figure 1:
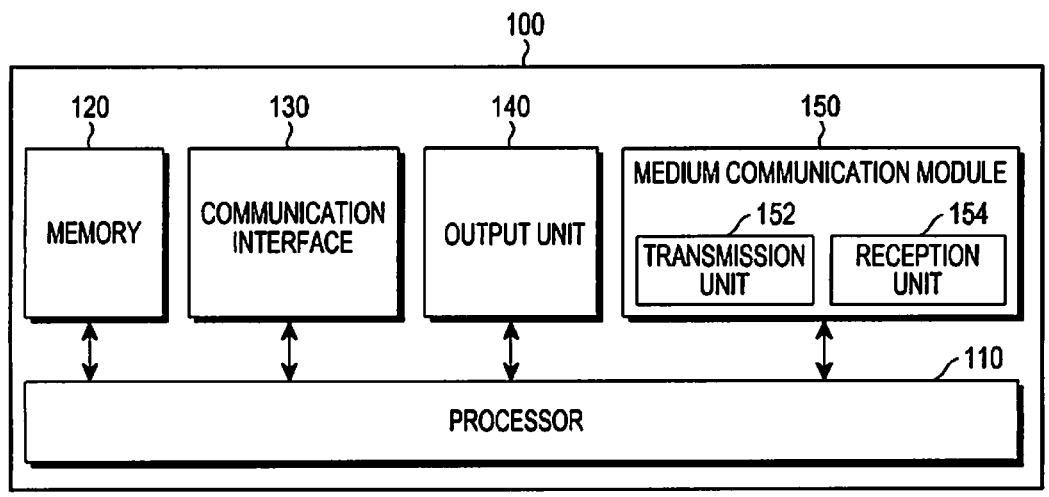
FIG. 1 is a block diagram illustrating a configuration of an electronic apparatus according to embodiments of the present invention.

The following description with reference to the accompanying drawings is provided to assist in a comprehensive understanding of embodiments of the invention as defined by the claims and their equivalents. It includes various specific details to assist in that understanding but these are to be regarded as mere examples. Accordingly, those of ordinary skill in the art will recognize that various changes and modifications of the embodiments described herein can be made without departing from the scope and spirit of the invention. The same or similar components may be designated by the same or similar reference numerals although they are illustrated in different drawings. In addition, descriptions of well-known functions and constructions may be omitted for clarity and conciseness.

The terms and words used in the following description and claims are not limited to their dictionary meanings, but are merely used to enable a clear and consistent understanding of the invention. Accordingly, the following description of embodiments of the present invention is provided for illustration purposes and does not limit the scope of the invention as defined by the appended claims and their equivalents.

Herein, the singular forms "a," "an," and "the" include plural referents unless the context clearly dictates otherwise. Thus, for example, reference to "a component surface" includes reference to one or more of such surfaces.

Although the terms including ordinal numbers such as first and second may be used herein to describe various elements, these elements should not be limited by these terms. These terms are only used to distinguish one element from another. For example, a first element could be termed a second element, and similarly, a second element could be termed a first element, without departing from the scope of the present invention. The terminology used herein is for the purpose of describing particular embodiments of the present invention, and does not limit the scope of the present invention. As used herein, the term "and/or" includes any and all combinations of one or more of the associated listed items.

Methods of controlling an electronic apparatus according to embodiments of the present invention use medium communication. For example, a transmission unit of the electronic apparatus according to various embodiments of the present invention transmits a signal through a medium, and a reception unit thereof receives the signal transmitted through the medium. The signal is periodically transmitted. In the medium, multiple transmission paths are formed by the signal travelling through the medium. For example, the straight line which connects the transmission unit to the reception unit forms a short transmission path. By contrast, for example, a long transmission path in the shape of a curve may also be formed connecting the transmission unit to the reception unit. The reception of the signal passing through the long transmission path will be more delayed than that of the signal passing through the short transmission path. Moreover, the former will have a weaker strength than the latter.

An electronic apparatus according to embodiments of the present invention selects at least some signals, which are to be used to control the electronic apparatus, from among signals transmitted through the medium. The electronic apparatus compares the signals with a predetermined signal. For example, an electronic apparatus according to an embodiment of the present invention may compare a pattern of each signal with that of a predetermined signal. The predetermined signal comprises at least one signal. When some signals are related to the predetermined signal, the electronic apparatus performs an operation according to the predetermined signal.

Examples of signals used for communication through a medium include an electromagnetic wave, a sound wave (e.g., an ultrasonic wave or a bone conduction signal), and the like. One medium communication technology using an electromagnetic wave, for example, is Electric Field Communication (EFC) technology. EFC is a communication technology which can be used for transmitting a signal through a human body, by sensing a change in an electric field induced in the dielectric substance being used as the medium (e.g., water or a human body).

Signals transmitted through various paths in the medium are distinguished from each other using a reception time point of a signal as a reference in embodiments of the present invention. Signals with as much transmission speed as a first received signal are distinguished from signals received with a delay using a time band according to embodiments of the present invention.

Hereinafter, embodiments of the present invention will be described with reference to the accompanying drawings.

FIG. 1 is a block diagram illustrating a configuration of an electronic apparatus according to embodiments of the present invention.

Referring to FIG. 1, an electronic apparatus 100 according to various embodiments of the present invention includes a processor 110, a memory 120, a communication interface 130, an output unit 140, and a medium communication module 150. The electronic apparatus 100 may be an electronic apparatus having at least two parts which contact a human body. The electronic apparatus 100 may be a wearable electronic apparatus. For example, the electronic apparatus 100 may be implemented as an electronic apparatus using eyeglasses, clothes, a helmet, a watch, or the like.

The processor 110 controls the elements of the electronic apparatus 100, and processes data (e.g., multimedia data) received from the communication interface 130 and provides the processed data to the output unit 140. The processor 110 processes a signal received from the medium communication module 150. According to an embodiment of the present invention, the processor 110 sets a function according to the received signal. The processor 110 matches a function to a pattern formed by signals within a set time period among received signals. The processor 110 controls the memory 120 to store functions according to received signals and/or functions matched to patterns formed by multiple received signals.

According to an embodiment of the present invention, the processor 110 performs a function according to the received signal. The processor 110 performs the function which matches the pattern formed by signals received within a set time period. The processor 110 performs the function according to the received signal or the function matched to the pattern formed by the multiple received signals, with reference to the memory 120. According to an embodiment of the present invention, the processor 110 selects some signals from among the received signals, and sets or performs a function according to the selected signals.

The memory 120 provides data requested by the processor 110, and stores data processed by the processor 110. According to an embodiment of the present invention, the memory 120 stores a function matched to a pattern formed by at least one signal. For example, a first function is matched to a first pattern, and a second function is matched to a second pattern.

The communication interface 130 exchanges data between an external device (e.g., various user devices such as a computer, a server, a smart phone, etc.) and the electronic apparatus 100 using wireless communication (e.g., Wi-Fi, Bluetooth) or wired communication.

The output unit 140 outputs data processed by the processor 110. For example, the output unit 140 may be a speaker, a display, a hologram projector, and the like.

The medium communication module 150 transmits and receives signals through the medium. The medium communication module 150 includes a transmission unit 152 for transmitting a signal through the medium and a reception unit 154 for receiving a signal through the medium. The transmission unit 152 and the reception unit 154, for example, may contact the medium or may be located nearby the medium, in order to transmit and receive signals through the medium.

Figure 2:
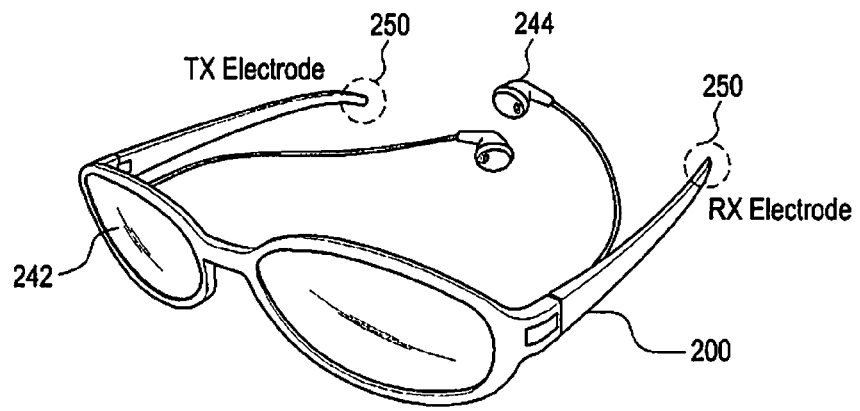
FIG. 2 is a view illustrating eyeglasses as an example of an electronic apparatus according to embodiments of the present invention.

FIG. 2 illustrates eyeglasses as an example of an electronic apparatus according to embodiments of the present invention. Referring to FIG. 2, eyeglasses 200 capable of performing communication through the medium include a medium communication module 250, eyeglass lenses 242, and an earphone 244. The eyeglasses 200 are an example of the electronic apparatus 100 illustrated in FIG. 1. The medium communication module 250, for example, corresponds to the medium communication module 150 illustrated in FIG. 1.

The medium communication module 250 disposed within the eyeglasses 200 enable the eyeglasses 200 to transmit and receive signals through a human body with which the eyeglasses 200 are in contact. According to an embodiment of the present invention as illustrated in FIG. 2, the medium communication module 250 is disposed at the end of each of the eyeglass temples. The medium communication module 250 includes a transmission unit for transmitting a signal and a reception unit for receiving a signal. The transmission unit is disposed at the end of the right eyeglass temple, and the reception unit is disposed at the end of the left eyeglass temple. When an electromagnetic wave is used as a signal for medium communication, a transmission electrode (TX Electrode) at the end of the right eyeglass temple enables contact between the transmission unit and the human body, and a reception electrode (RX Electrode) at the end of the left eyeglass temple enables contact between the reception unit and the human body.

The eyeglass lenses 242, for example, may be a unit for outputting an image. When a user wears the eyeglasses 200, the user can view an image displayed on the eyeglass lenses 242.

The earphone 244, for example, may be a unit for outputting sound, such as a voice.

A processor processes a signal from the medium communication module 250, and controls operations of the eyeglasses 200. For example, the processor controls the magnitude of a voice to be output from the sound output unit, according to a signal from the medium communication module 250. Also, for example, the processor converts an image to be output from the image output unit, according to a signal from the medium communication module 250. The above-described eyeglasses 200 are an example of the electronic apparatus 100 according to one of various embodiments of the present invention, and control operations of the processor are not limited to the above-described control operations. For example, the processor, the memory and the communication interface may be integrated into the eyeglass temples or the front frame of the eyeglasses 200. According to various embodiments of the present invention, the electronic apparatus includes a transmission unit that transmits a first signal to a first part of a medium, a reception unit that receives second signals corresponding to the first signal through a second part of the medium, and a control unit that selects at least some signals from among the second signals and sets a function according to the selected signals. Here, the second signal refers to the first signal as modified by being transmitted through each of various paths of the medium.

According to embodiments of the present invention, the control unit adjusts an operation of the electronic apparatus based on a set function.

According to embodiments of the present invention, the transmission unit transmits the first signal during each set time period.

According to embodiments of the present invention, when each time period includes a sub-time period within which strengths of the second signals differ from the strength of a reference signal, the control unit selects signals within that sub-time period.

According to embodiments of the present invention, the control unit adjusts one or more time periods during which the strength of the first signal or the first signal is transmitted.

According to embodiments of the present invention, the electronic apparatus includes a memory which stores a sub-time period, within which the effective signals exist, among sub-time periods included in each time period or which stores a pattern of the effective signals and a function matched to the pattern.

According to embodiments of the present invention, the transmission unit or the reception unit transmits or receives a signal through a medium which may be at least one of a human body, an organism, inorganic matter and metal.

According to embodiments of the present invention, the electronic apparatus receives signals transmitted through multiple transmission paths formed in the medium.

Figure 3:
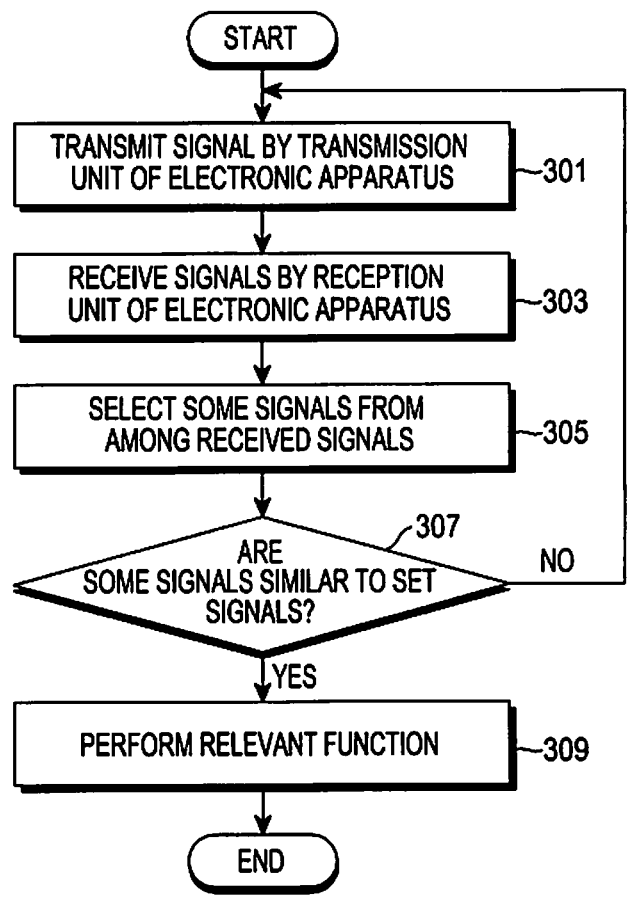
FIG. 3 is a flowchart illustrating a control method of an electronic apparatus according to embodiments of the present invention.

FIG. 3 is a flowchart illustrating a control method of an electronic apparatus according to embodiments of the present invention. In step 301, the transmission unit (e.g., transmission unit 152) of the electronic apparatus (e.g., electronic apparatus 100) transmits a signal to a first part of the medium. The transmission unit of the electronic apparatus, for example, may be the transmission unit of the medium communication module (e.g., medium communication module 150).

The medium is at least one of a human body, an organism, inorganic matter and metal. Multiple transmission paths are formed by the signal travelling through the medium. For example, when the medium is the human body, multiple transmission paths may be formed as illustrated in FIG. 4.

Figure 4:
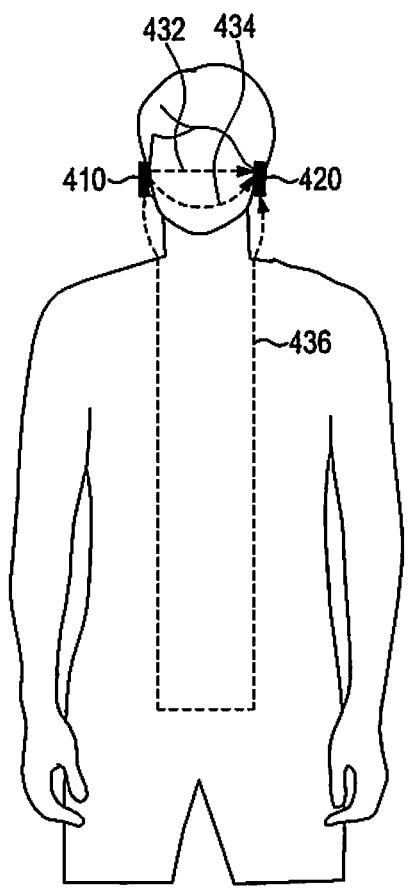
FIG. 4 is a view illustrating an example of multiple paths, through each of which a signal can be transmitted within a human body according to embodiments of the present invention.

FIG. 4 illustrates some of the multiple paths through which a signal can be transmitted within a human body. Referring to FIG. 4, transmission unit 410 (e.g., transmission unit 152) of the electronic apparatus (e.g., electronic apparatus 100) has transmitted a signal which passes through each of various transmission paths 432, 434 and 436 formed in the human body before arriving at the reception unit 420 (e.g., reception unit 154) of the electronic apparatus. The signals can be transmitted along the surface of or inside the medium. The signal may be an electrical signal or a sound wave. The signal may be transmitted, for example, in each cycle.

Referring again to FIG. 3, in step 303, the reception unit (e.g., reception unit 152) of the electronic apparatus receives signals through a second part of the medium. Signals that the reception unit of the electronic apparatus receives include signals received through the multiple paths formed in the medium.

In step 305, the processor (e.g., processor 110) of the electronic apparatus selects some signals as effective signals from among the signals that the reception unit of the electronic apparatus has received from the second part of the medium. These signals may correspond to when an operation mode of the electronic apparatus is selected or a set function is performed. When signals are received through multiple paths formed in the medium, the accuracy of reception can be improved by reducing weights of signals which do not have to be considered in selecting a mode of the electronic apparatus or performing a set function thereof.

In step 307, the processor of the electronic apparatus determines whether the selected signals are similar to set signals and/or whether a pattern of the selected some signals is similar to that of the set signals.

In step 309, the processor of the electronic apparatus performs a control operation for performing a function or entering a set operation mode according to the selected signals. These signals are selected by various methods.

Figure 5A:
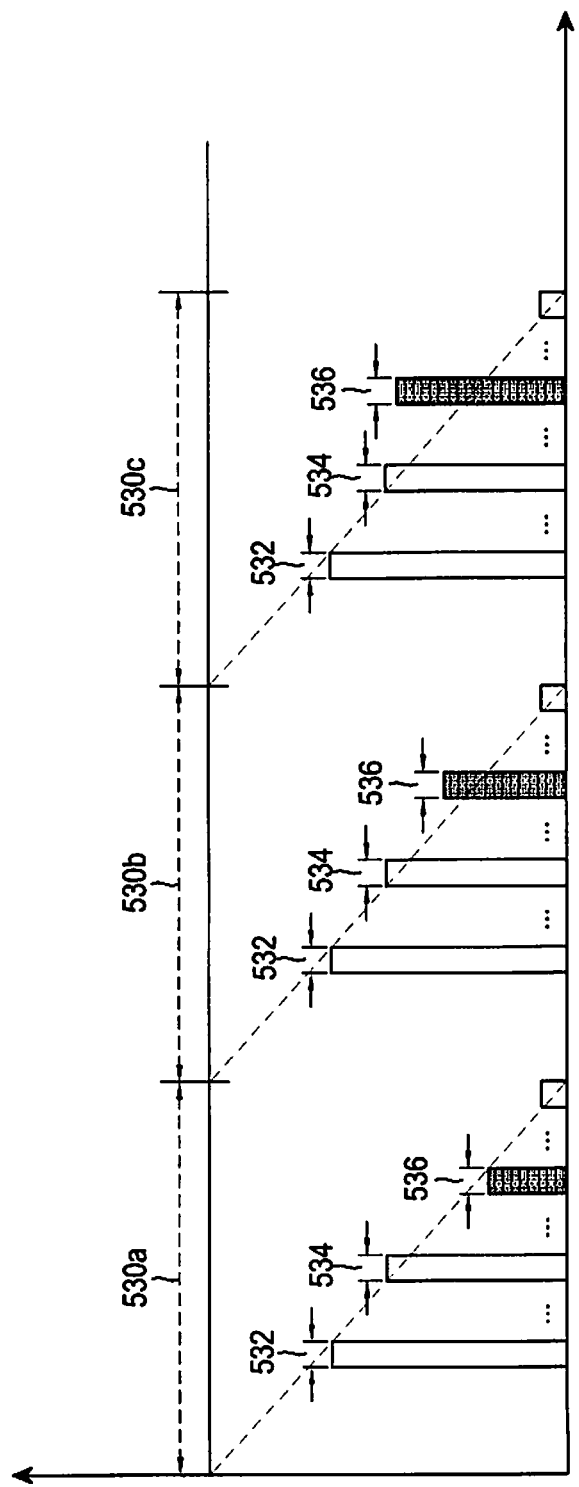
FIGS. 5A and 5B are views illustrating a method of selecting a signal according to embodiments of the present invention.
Figure 5B:
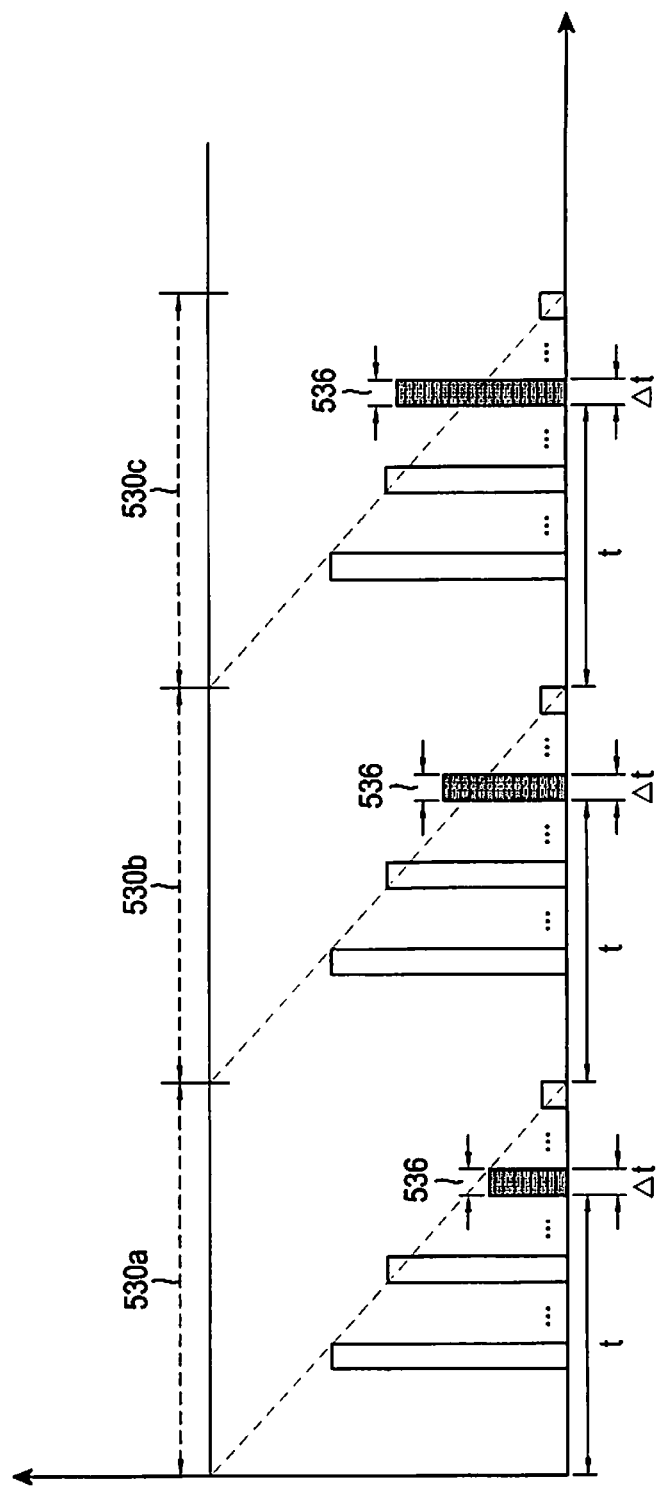

FIGS. 5A and 5B are views illustrating a method of selecting signals according to embodiments of the present invention. FIGS. 5A and 5B show signals received by the reception unit (e.g., reception unit 154) of the electronic apparatus (e.g., electronic apparatus 100) when signals are transmitted and received during each set time period. In FIGS. 5A and 5B, each of time periods 530a, 530b and 530c include at least one sub-time period (e.g., sub-time periods 532, 534 and 536).

The processor (e.g., processor 110) of the electronic apparatus, for example, compares signals received during one or more sub-time periods within a set time period with those received during the same one or more sub-time periods of another set time period. The processor of the electronic apparatus selects the signals within each sub-time period whose signal strength has changed. For example, as shown in FIG. 5A, when the strength of signals received during sub-time period 536 within time period 530a are different from those of signals received during the same sub-time period 536 within time period 530b, the processor of the electronic apparatus selects the signals received during each sub-time period 536 as the effective signals.

According to an embodiment of the present invention, the processor of the electronic apparatus selects at least one sub-time period from among sub-time periods existing within each set time period, and selects signals existing within the at least one selected sub-time period. The at least one selected sub-time period may be a time period during which a signal is transmitted through a desired transmission path from among multiple transmission paths formed in the medium. The at least one selected sub-time period may have already been stored in the memory 120 of the electronic apparatus.

For example, when signals are received during time periods 530a, 530b and 530c as shown in FIG. 5B, the processor of the electronic apparatus selects sub-time period 536 within each of the time periods 530a, 530b and 530c, and selects the signals received during the selected sub-time period 536 of each of the time periods 530a, 530b and 530c. In this example, the processor of the electronic apparatus selects signals that the reception unit of the electronic apparatus receives during a set time interval Δt starting from a time point which is a set time interval t from when the signal was transmitted by the transmission unit of the electronic apparatus.

Hereinabove, the control method of the electronic apparatus using the medium communication according to embodiments of the present invention has been described with reference to FIGS. 1 to 5B. In order to perform a function which is set according to the received signals, it is possible to set what function is to be performed according to a pattern of the received signals.

Figure 6:
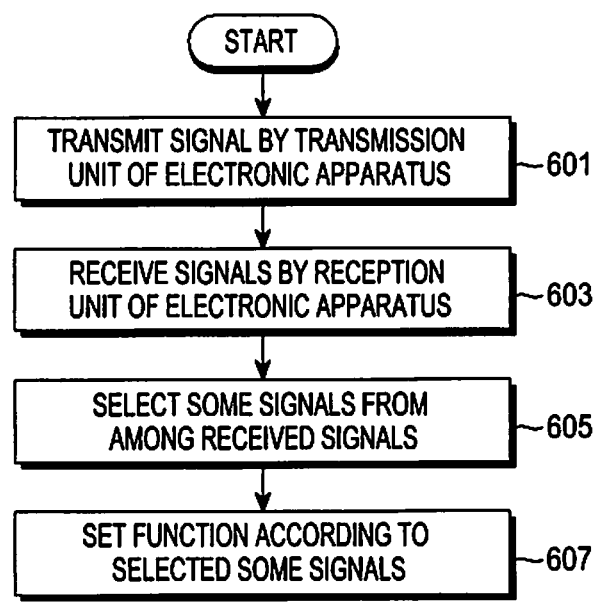
FIG. 6 is a flowchart illustrating a method of controlling an electronic apparatus according to embodiments of the present invention.

FIG. 6 is a flowchart illustrating a method of controlling an electronic apparatus according to embodiments of the present invention.

In step 601, the transmission unit (e.g., transmission unit 152) of the electronic apparatus (e.g., electronic apparatus 100), for example, transmits a signal to the first part of the medium. The signal, for example, may be transmitted when a transmission path formed in the medium has changed, or when a new transmission path has formed in the medium. Step 601 is described in detail below with reference to FIGS. 4 and 7.

Figure 7:
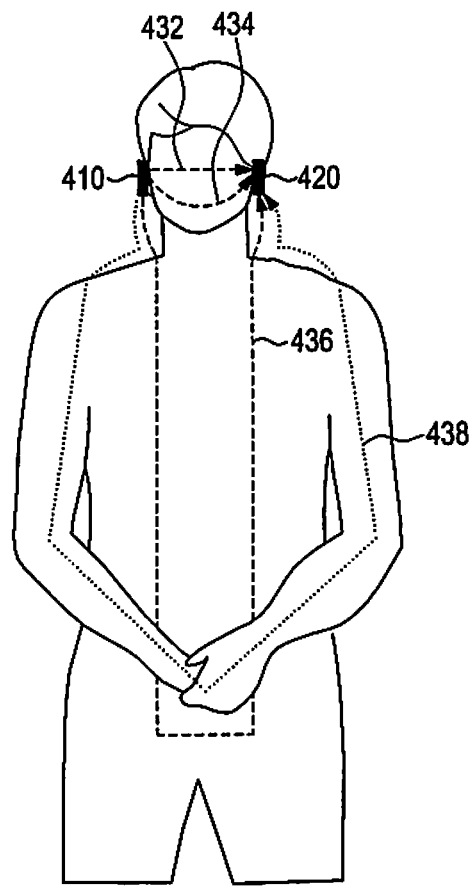
FIG. 7 is a view illustrating an example of a change in a transmission path formed in a medium according to embodiments of the present invention.

FIG. 7 is a view illustrating an example of a change in a transmission path formed in a medium according to various embodiments of the present invention. Transmission paths through a user's body may be changed depending on a change in action and/or posture of the user. For example, the signal transmitted in FIG. 4 forms the multiple transmission paths 432, 434 and 436, but the same signal transmitted in FIG. 7, where the user has changed posture, forms at least one additional transmission path 438 as shown in FIG. 7. In various embodiments of the present invention, a change in transmission path includes at least when the length of a previously-formed transmission path changes, when a new transmission path is formed, and when an existing transmission path ceases to exist. The electronic apparatus may guide the user to take a particular action in order to change a transmission path. For example, the electronic apparatus may provide the user with a guide message guiding the user to take a particular action, where the guide message is provided by outputting text, a voice, an image, vibration, or the like. When the electronic apparatus receives a set response from the user or after a set time period passes, the electronic apparatus transmits a signal. The signal is periodically transmitted.

Referring again to FIG. 6, in step 603, the reception unit (e.g., reception unit 154) of the electronic apparatus, for example, receives signals through a second part of the medium.

In step 605, the processor (e.g., processor 110) of the electronic apparatus selects some signals from among the signals received through the medium. These signals are selected as described above with reference to FIG. 5A.

In embodiments of the present invention, the processor of the electronic apparatus performs a control operation for storing a sub-time period, during which the selected some signals have been received. The stored sub-time period, is used to select some signals for performing a set function, as described above with reference to FIG. 5B. In embodiments of the present invention, an operation of selecting a sub-time period includes comparing signals received during at least one sub-time period of a set time period with those received during the same at least one sub-time period of another set time period, determining based on a result of the comparison whether there exists a sub-time period within which signal strengths have changed from one set time period to another, and selecting the sub-time period of each set time period within which the signal strengths have varied.

Figure 8A:
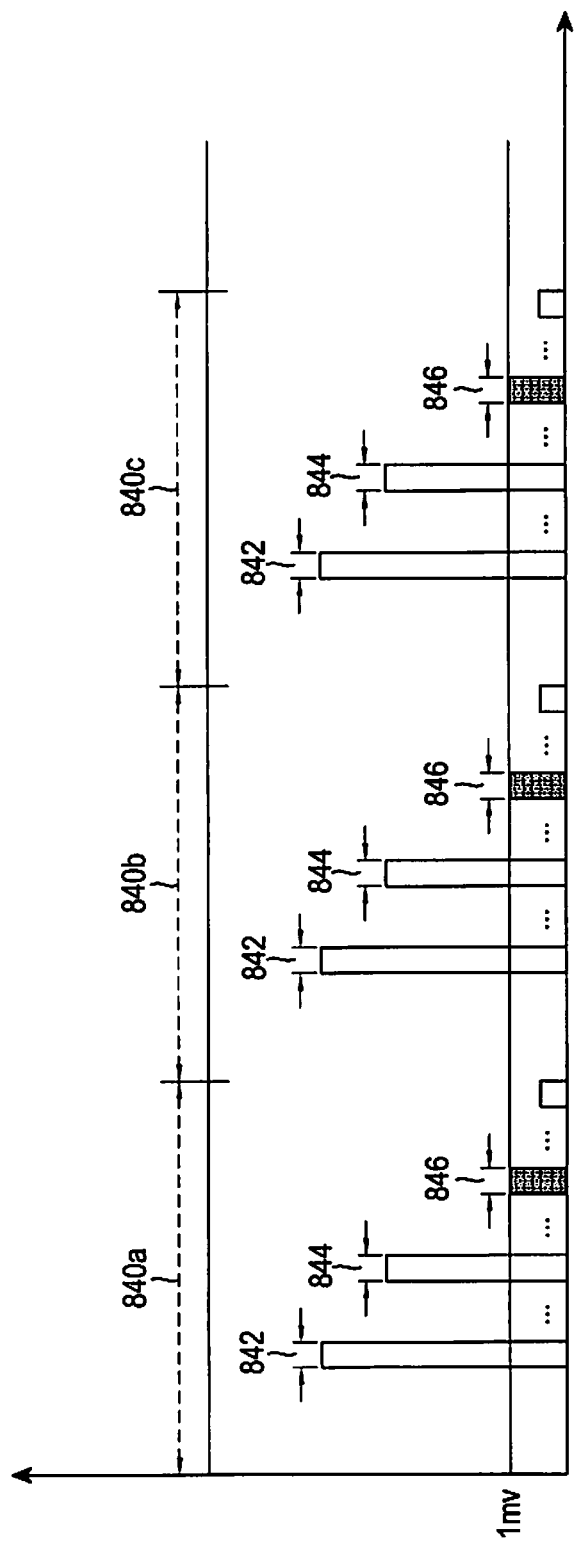
FIGS. 8A to 9D illustrate examples of selecting a sub-time period according to embodiments of the present invention.
Figure 8B:
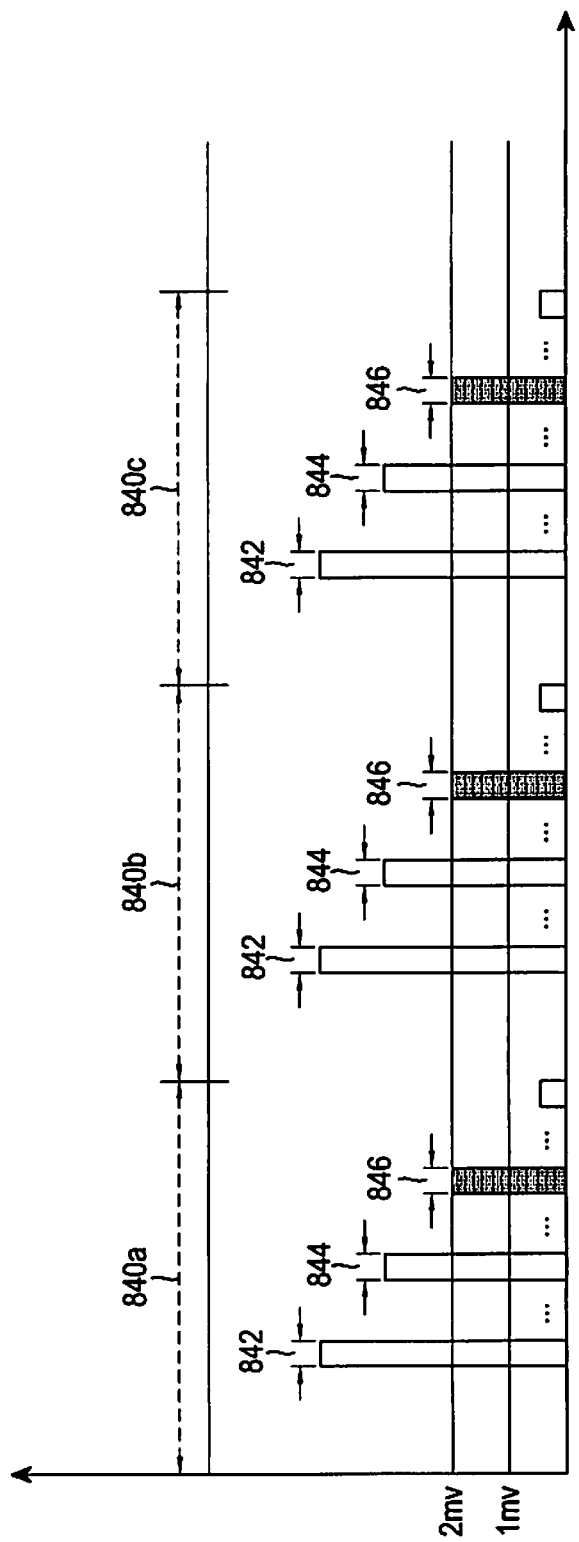

The operation of selecting a sub-time period is described below with reference to FIG. 4, FIG. 7, and FIGS. 8A and 8B. FIGS. 8A and 8B are views illustrating examples of selecting an effective sub-time period according to embodiments of the present invention. For example, when the user performs a first action, transmission paths are formed as illustrated in FIG. 4. Signals received during each set time period are shown in FIG. 8A. Signals received during each sub-time period 842 in FIG. 8A are signals received through the transmission path 432 in FIG. 4, signals received during each sub-time period 844 in FIG. 8A are signals received through the transmission path 434 in FIG. 4, and signals received during each sub-time period 846 in FIG. 8A are signals received through the transmission path 436 in FIG. 4. When the user performs a second action, there is a change in transmission paths as shown in FIG. 7. Signals which are received during each set time period are changed, as shown in FIG. 8B. In FIG. 7, a signal transmitted through the transmission path 436 has delay time similar to that of a signal transmitted through the transmission path 438. The processor (e.g., processor 110) of the electronic apparatus (e.g., electronic apparatus 100) compares signals, which are matched to the user's first action and are received during at least one sub-time period (e.g., sub-time periods 842, 844 and 846) of each of the time periods 840a, 840b and 840c in FIG. 8A, with signals which are matched to the user's second action and are received during the at least one sub-time period (e.g., sub-time periods 842, 844 and 846) of each of the time periods 840a, 840b and 840c in FIG. 8B, determines based on a result of the comparison whether there exists a sub-time period in each of the time periods 840a, 840b and 840c within which signal strength has changed, and selects the sub-time period of each of the time periods 840a, 840b and 840c within which the signal strength has changed, as an effective sub-time period.

From FIGS. 8A and 8B, it can be seen that the signal strength has changed within sub-time period 846. The change in signal strength may be caused by forming the transmission path 438. As described above, a signal transmitted through the transmission path 436 has a time delay similar to that of a signal transmitted through the transmission path 438. Accordingly, the strength of the signals which have passed through the transmission paths 436 and 438 are added together within each sub-time period 846 in FIG. 8B, and the added strength is detected to be larger than before, i.e., than within each sub-time period 846 in FIG. 8A. The processor of the electronic apparatus selects each sub-time period 846 as an effective sub-time period. According to various embodiments of the present invention, the operation of selecting an effective sub-time period may be performed while a transmission path formed in the medium is continuously changed. The operation of selecting an effective sub-time period will be described below with reference to FIG. 9. FIGS. 9A to 9D are views illustrating examples of selecting a sub-time period according to embodiments of the present invention.

Figure 9A:
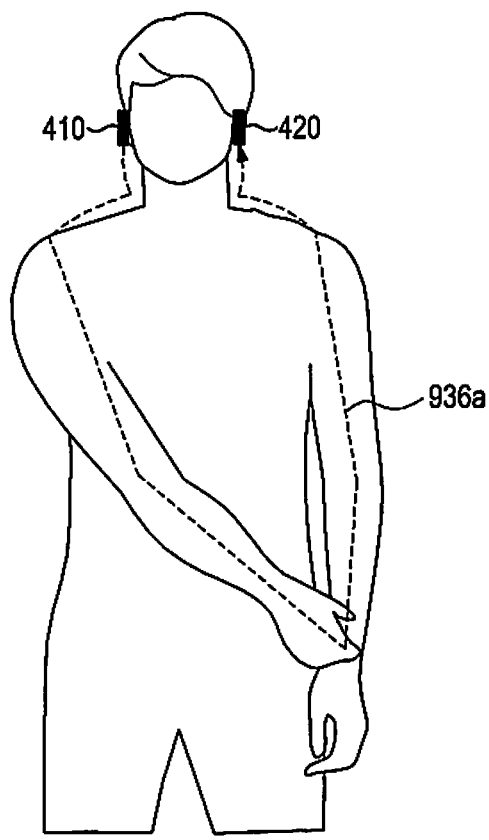
Figure 9B:
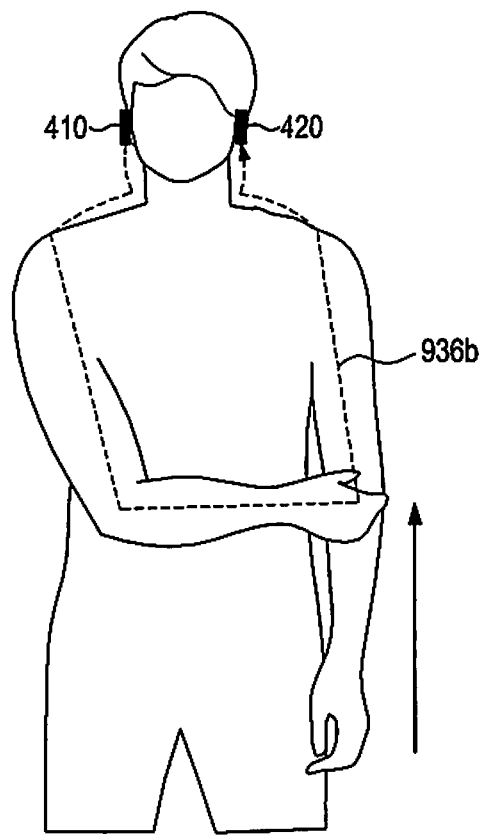
Figure 9C:
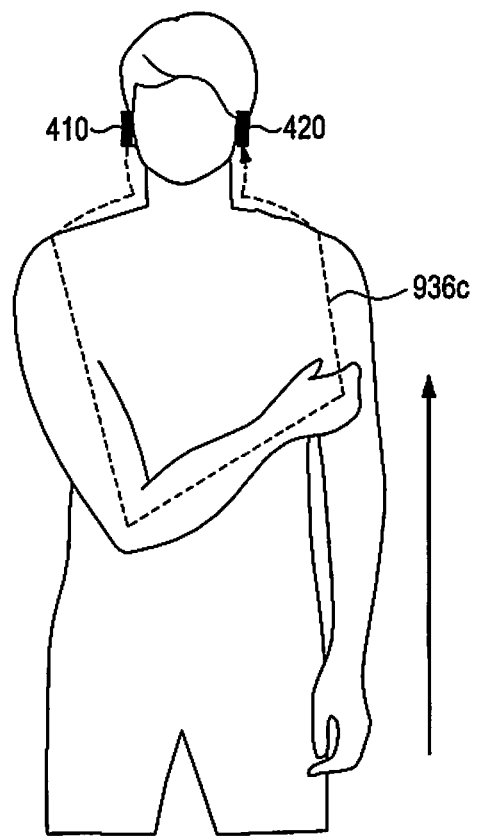
Figure 9D:
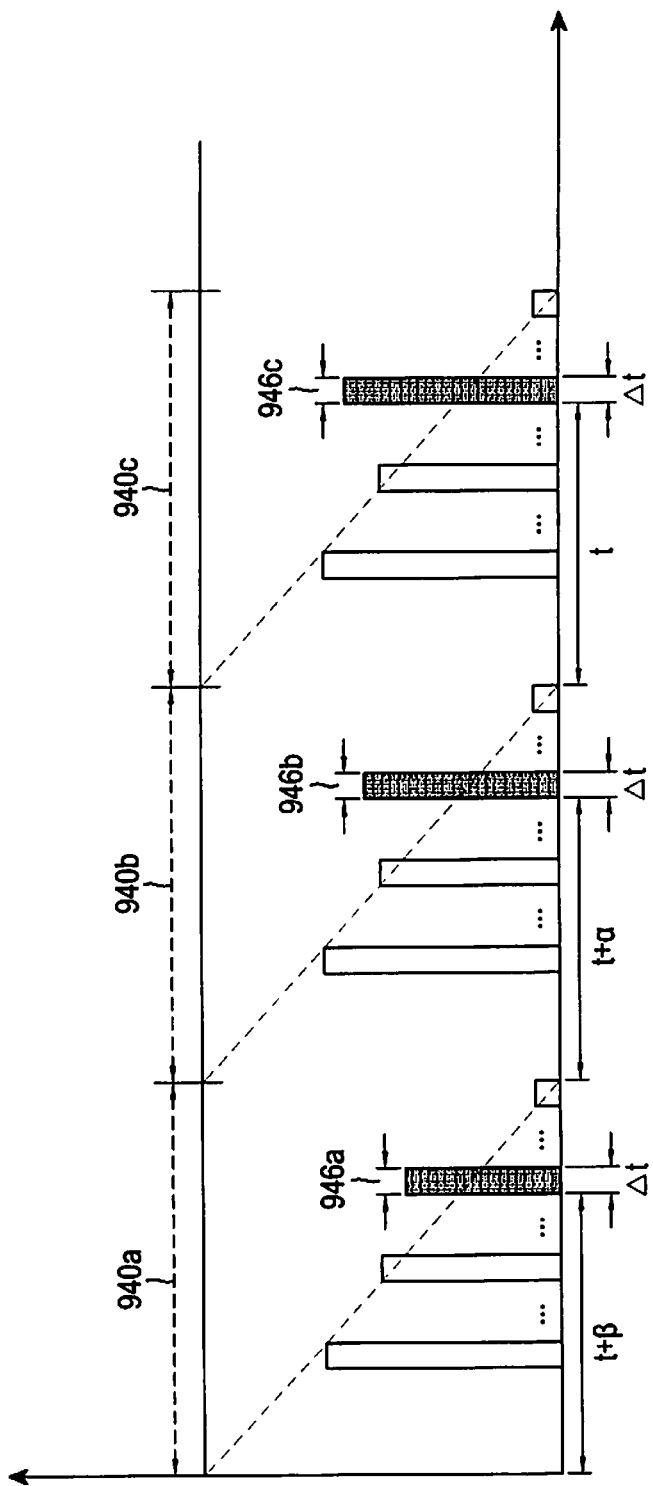

FIGS. 9A to 9D illustrate when, due to actions o the user, transmission path 936a shown in FIG. 9A is first changed to transmission path 936b shown in FIG. 9B and is then changed to transmission path 936c shown in FIG. 9C. Transmission paths 936a, 936b and 936c have different time delays. Referring to FIG. 9D, during time period 940a, signals are received when transmission path 936a shown in FIG. 9A has been formed. During time period 940b in FIG. 9D, signals are received when transmission path 936b has formed, as shown in FIG. 9B. During time period 940c in FIG. 9D, signals are received when transmission path 936c has formed, as shown in FIG. 9C.

Within each of sub-time periods 946a, 946b and 946c as shown in FIG. 9D, a signal transmitted through a newly-formed transmission path is added to a signal transmitted through an existing transmission path, and thus the strength of the added signals is detected to be larger than before. For example, within the sub-time period 946a, a signal transmitted through the transmission path 936a formed due to the action of the user as shown in FIG. 9A is added to a signal transmitted through an existing transmission path (e.g., transmission path 436 in FIG. 4) having a time delay similar to that of the transmission path 936a, and thus the strength of the added signals is detected to be larger than before. Signals within the sub-time period 946a are received during a time interval $\Delta t$ which starts after a time interval $t+\beta$ passes from a time point when the time period 940a has begun. Signals within the sub-time period 946b are received during a time interval $\Delta t$ which starts after a time interval $t+\alpha$ passes from a time point when the time period 940b has begun. Signals within the sub-time period 946c are received during a time interval $\Delta t$ which starts after a time interval of t passes from a time point when the time period 940c has begun.

In the present example, the signals received within the sub-time period 946a had a longer transmission path than the signals received within the sub-time period 946b, and thus were received later within time period 940a than the signals received during sub-time period 946b within time period 940b. The signals received within the sub-time period 946b in turn had a longer transmission path than the signals received within the sub-time period 946c, and thus were received later within time period 940b than the signals received during sub-time period 946c in time period 940c. In other words, the time interval $t+\beta$ is longer than the time interval $t+\alpha$, and the time interval $t+\alpha$ is longer than the time interval t. The processor (e.g., processor 110) of the electronic apparatus (e.g., electronic apparatus 100) sets an effective sub-time period in such a manner as to include the multiple sub-time periods 946a, 946b and 946c, within each of which the signal strength changed when at least one transmission path changed. For example, the processor of the electronic apparatus sets a time interval $\beta+\Delta t$ starting from a time point when each of the time periods 940a, 940b and 940c has begun and the time interval oft passes, as an effective sub-time period. In the present example, the time interval of t may refer to a time interval from a time point when the transmission unit of the electronic apparatus has transmitted a signal, to a time point when the reception unit of the electronic apparatus receives the same signal.

Referring again to FIG. 6, in step 607, the processor of the electronic apparatus sets a function according to the selected signals. The selected signals, for example, may be multiple signals. In embodiments of the present invention, the processor of the electronic apparatus sets a function matched to a pattern of selected signals. The functions are related, for example, to image control, volume control, the switching of an operation mode, and the like. The functions may be different depending on an operation mode of the electronic apparatus. For example, when the electronic apparatus is in media reproduction mode, the function is related to image control or volume control. For example, when the electronic apparatus is in electronic book mode, the function is related to a bookmark setting, a bookmark release, or a page shift.

FIG. 10 is a view illustrating examples of functions matched to patterns of signals, according to embodiments of the present invention. In FIG. 10, the pattern of signals to which a function is matched is received during at least one effective sub-time period. Also, for convenience of description, only the signals received within the effective sub-time period are illustrated in FIG. 10.

In FIG. 10, it can be seen that a different signal pattern corresponds to each action of the user detected by the electronic apparatus, and a corresponding function is mapped to each signal pattern. The electronic apparatus stores each signal pattern and the function matched to each signal pattern. The user may select the functions from among multiple menu lists.

According to embodiments of the present invention, when the signal strength of a signal transmitted by the transmission unit (e.g., transmission unit 152) of the electronic apparatus (e.g., electronic apparatus 100) is small, an effective signal may not be detected among the signals received by the reception unit of the electronic apparatus. The strengths of the various signals received by the reception unit of the electronic apparatus differ from each other depending on the characteristics (e.g., the size and material) of the medium. The electronic apparatus adjusts the strength of a transmitted signal so that the signals for setting and/or performing each function can be detected. For example, when a person of small build uses the electronic apparatus capable of medium communication through the human body, a path through which a signal is transmitted has a short length, and the reduction in signal strength is small when the signal is received. Accordingly, although the strength of a transmitted signal is small, an effective signal can be detected. In contrast, when a person of large build uses the electronic apparatus, a path through which a signal is transmitted has a long length, and a reduction in the signal strength is large when the signal is received. When the strength of the transmitted signal is small, an effective signal may not be detected. Accordingly, the strength of the transmitted signal is increased in order to make it possible to detect an effective signal when it is received. For example, the processor of the electronic apparatus may control the transmission unit to vary the strength of the signal. When the processor senses that the reception unit of the electronic apparatus has received a signal having a strength large enough to be processed, the processor of the electronic apparatus (e.g., processor 110) sets the strength of the signal that the transmission unit of the electronic apparatus transmits as the current value, or a strength greater than the current value, for subsequent operations.

According to embodiments of the present invention, the electronic apparatus (e.g., electronic apparatus 100) transmits and receives signals having a set pulse shape, and thereby distinguishes signals received from other sources and/or through another medium from its own signal and selects effective signals from among its own signals. This configuration will be described below with reference to FIG. 11.

Figure 11:
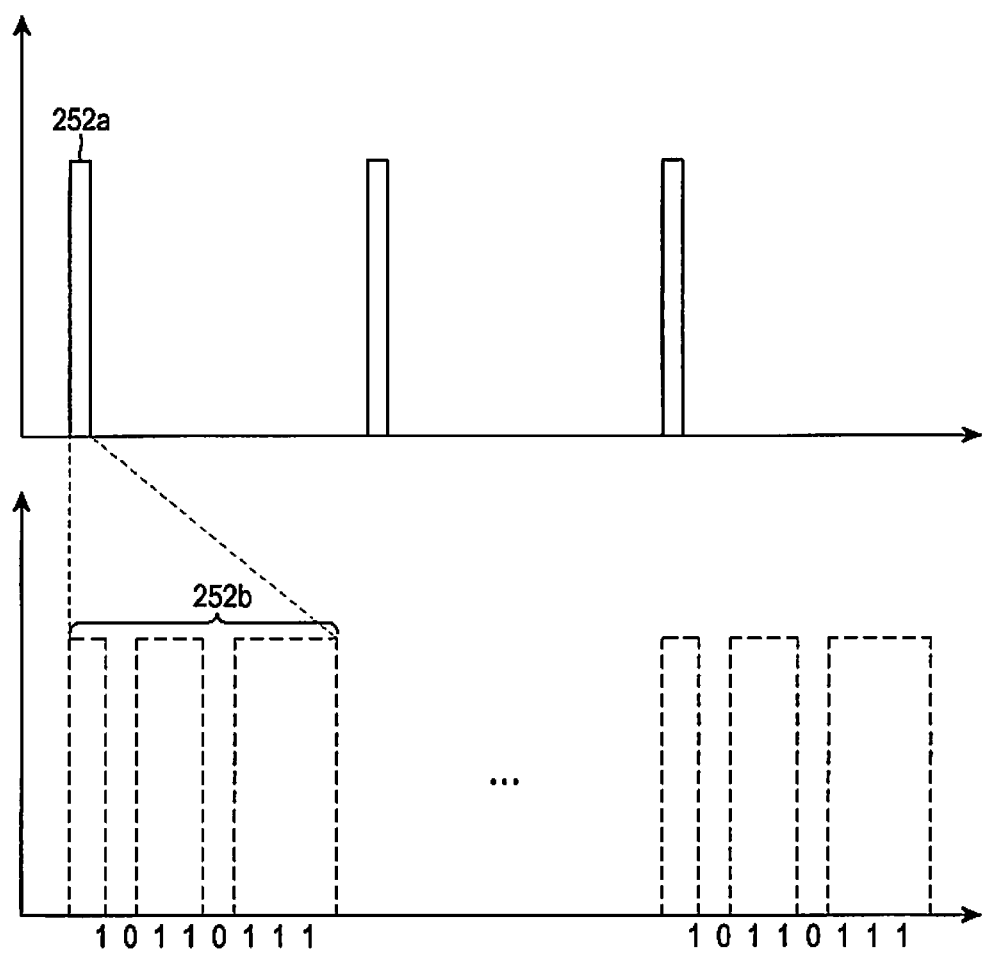
FIG. 11 is a view illustrating an example of pulse-shaped signals according to embodiments of the present invention.

FIG. 11 is a view illustrating an example of pulse-shaped signals according to embodiments of the present invention. The electronic apparatus may transmit and receive a signal 252a in the form of one pulse as shown in the upper part of FIG. 11. Otherwise, the electronic apparatus may transmit and receive a signal 252b in the form of multiple pulses as shown in the lower part of FIG. 11. The lower part of FIG. 11 enlarges the relevant time period for convenience of description. The signal 252b having such a pulse shape may be transmitted and received together with the signal 252a during a short time period.

When the electronic apparatus receives multiple signals, the electronic apparatus selects some signals from among the received signals, for example, where the signals all have a pulse shape identical to the signal transmitted by the electronic apparatus. For example, when a signal that the transmission unit of the electronic apparatus has transmitted includes a pulse train representing "10110111" and the reception unit of the electronic apparatus receives two signals which include the pulse trains representing "10110111" and "11100111," the processor of the electronic apparatus selects the signal including the pulse train representing "10110111" from among the two received signals, as the effective signals.

According to embodiments of the present invention, the method of controlling the electronic apparatus includes transmitting a first signal to a first part of a medium, receiving second signals corresponding to the first signal through a second part of the medium, selecting at least some signals from among the second signals, and performing, by the electronic apparatus, a function set according to the selected at least some signals.

According to embodiments of the present invention, the first signal is transmitted during each set time period.

According to embodiments of the present invention, each time period is set according to the signal transmission characteristics of the medium.

According to embodiments of the present invention, the strength of the first signal is set according to the signal transmission characteristics of the medium.

According to embodiments of the present invention, strengths of present second signals are compared with strengths of past second signals received before the present second signals, and at least some effective signals are selected from among the multiple past and present second signals.

According to embodiments of the present invention, strengths of signals within sub-time periods included in one time period of the second signals are compared with strengths of signals within sub-time periods included in another time period of the second signals, and signals within at least one of the sub-time periods of the one and another time periods are selected as the at least some effective signals.

According to embodiments of the present invention, signals within a predetermined sub-time period of multiple sub-time periods included in each time period of the second signals are selected as the at least some effective signals.

According to embodiments of the present invention, a pattern that the at least some effective signals form is determined, and a predetermined function matched to the determined pattern is performed.

According to embodiments of the present invention, when a function according to the at least some effective signals is not set, the function is set. According to embodiments of the present invention, the function matched to a pattern of the at least some effective signals is predetermined.

The embodiments of the present invention as described above may be implemented by various optional methods. For example, the embodiments of the present invention may be implemented in hardware, software, or a combination of hardware and software. When the embodiments of the present invention are implemented in software, the embodiments of the present invention may be implemented in software executed by one or more processors using various operating systems or various platforms. In addition, this software may be written by using any programming language among multiple appropriate programming languages. Also, this software may be compiled into an executable machine language code or intermediate code, which is executed by a framework or a virtual machine.

Also, when the embodiments of the present invention are executed by one or more processors, the embodiments of the present invention may be implemented by using processor-readable mediums (e.g., a memory, a floppy disk, a hard disk, a compact disk, an optical disk, and a magnetic tape) for recording one or more programs for performing the methods which implement the various embodiments of the present invention as discussed above.

The methods according to embodiments of the present invention can control the electronic apparatus, with low power consumption by using medium communication.

Also, the methods according to embodiments of the present invention can control the electronic apparatus regardless of the environment by using medium communication.

Further, the method of controlling an electronic apparatus, and the electronic apparatus using the same, according to embodiments of the present invention, can improve the speed of recognition of control commands when the electronic apparatus is controlled by using medium communication.

While the invention has been shown and described with reference to certain embodiments thereof, it will be understood by those skilled in the art that various changes in form and details may be made therein without departing from the spirit and scope of the present invention as defined by the appended claims and their equivalents.

What is claimed is:

1. A method of controlling an electronic apparatus, the method comprising:
   transmitting, by the electronic apparatus, a first signal to a first part of a medium;
   receiving, by the electronic apparatus, second signals through a second part of the medium, the second signals corresponding to the transmitted first signal;
   selecting, by the electronic apparatus, at least some signals from among the second signals; and
   if a function, which is used to automatically control at least one operation of the electronic apparatus, corresponding to the selected at least some signals has been set, performing, by the electronic apparatus, the function corresponding to the selected at least some signals,
   wherein performing the function according to the selected at least some signals comprises:
   determining a pattern formed by the selected at least some signals; and
   performing a predetermined function matched to the determined pattern.

2. The method of claim 1, wherein transmitting, by the electronic apparatus, the first signal to the first part of the medium comprises transmitting the first signal during each set time period.

3. The method of claim 2, further comprising:
   setting each time period for transmitting the first signal according to signal transmission characteristics of the medium.

4. The method of claim 1, further comprising:
   setting a strength of the first signal according to signal transmission characteristics of the medium.

5. The method of claim 1, wherein selecting at least some signals comprises:
   comparing strengths of second signals received in a present time period with strengths of second signals received in a past time period; and
   selecting at least some signals from among the second signals in both the present and past time periods based on a result of the comparison.

6. The method of claim 1, wherein selecting at least some signals comprises:
   comparing strengths of second signals received within sub-time periods in one time period with strengths of second signals received within sub-time periods in another time period; and
   selecting second signals received within at least one of the sub-time periods of both the one and another time periods as the at least some signals based on a result of the comparison.

7. The method of claim 1, wherein selecting at least some signals comprises:
   selecting signals received within a predetermined sub-time period of multiple sub-time periods included in each time period of receiving the second signals as the at least some signals.

8. The method of claim 1, further comprising:
   if the function corresponding to the selected at least some signals has not been set, setting the function corresponding to the selected at least some signals.

9. The method of claim 8, wherein setting the function comprises:
   setting the function as matched to a pattern formed by the selected at least some signals.

10. An electronic apparatus comprising:
    a transmission unit configured to transmit a first signal to a first part of a medium;
    a reception unit configured to receive second signals through a second part of the medium, the second signals corresponding to the first signal; and
    a control unit configured to select at least some signals from among the second signals and to set a function, which is used to automatically control at least one operation of the electronic apparatus, corresponding to the selected at least some signals or perform the function corresponding to the selected at least some signals,
    wherein the control unit, when setting or performing the function according to the selected at least some signals, determines a pattern formed by the selected at least some signals, and performs a predetermined function matched to the determined pattern.

11. The electronic apparatus of claim 10, wherein the control unit is further configured to adjust an operation of the electronic apparatus based on the function.

12. The electronic apparatus of claim 10, wherein the transmission unit is configured to transmit the first signal during each set time period.

13. The electronic apparatus of claim 10, wherein the control unit is configured to select signals within a sub-time period as the at least some signals when strengths of the second signals received within the sub-time period differ from a strength of a reference signal.

14. The electronic apparatus of claim 10, wherein the control unit is further configured to adjust at least one of time periods, during each of which a strength of the first signal or the first signal is transmitted.

15. The electronic apparatus of claim 10, further comprising:
    a memory configured to store a sub-time period, within which the selected at least some signals are received, among sub-time periods included in each time period.

16. The electronic apparatus of claim 10, further comprising:
    a memory configured to store the pattern of the selected at least some signals and the function matched to the pattern.

17. The electronic apparatus of claim 10, wherein the medium comprises at least one of a human body, an organism, inorganic matter and metal.

18. The electronic apparatus of claim 10, wherein the second signals are received from multiple transmission paths formed in the medium by the transmitted first signal.

19. A computer-readable non-transitory recording medium storing a program for executing the steps of:
    transmitting, by an electronic apparatus, a first signal to a first part of a medium;
    receiving, by the electronic apparatus, second signals through a second part of the medium, the second signals corresponding to the first signal;
    selecting, by the electronic apparatus, at least some signals from among the second signals; and
    if a function, which is used to automatically control at least one operation of the electronic apparatus, corresponding to the selected at least some signals has been set, performing, by the electronic apparatus, the function corresponding to the selected at least some signals if such a function has been set, or if the function corresponding to the selected at least some signals has not been set, setting, by the electronic apparatus, the function corresponding to the selected at least some signals, wherein setting or performing the function according to the selected at least some signals comprises:

determining a pattern formed by the selected at least some signals; and performing a predetermined function matched to the determined pattern.

\* \* \* \* \*